(12) United States Patent
Lamerichs et al.

(10) Patent No.: US 11,656,310 B2
(45) Date of Patent: May 23, 2023

(54) REAL-TIME FMRI

(71) Applicant: KONINKLIJKE PHILIPS N.V., Eindhoven (NL)

(72) Inventors: Rudolf Mathias Johannes Nicolaas Lamerichs, Liempde (NL); Stephan Heunis, Nuenen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/297,417

(22) PCT Filed: Nov. 20, 2019

(86) PCT No.: PCT/EP2019/081863
§ 371 (c)(1),
(2) Date: May 26, 2021

(87) PCT Pub. No.: WO2020/109095
PCT Pub. Date: Jun. 4, 2020

(65) Prior Publication Data
US 2022/0034984 A1    Feb. 3, 2022

(30) Foreign Application Priority Data
Nov. 29, 2018   (EP) .................................... 18209210

(51) Int. Cl.
*G01R 33/48* (2006.01)
*G01R 33/50* (2006.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC .............. G01R 33/4806; G01R 33/50; G01R 33/5615; G01R 33/56366; A61B 5/0042; A61B 5/055; A61B 5/4064
See application file for complete search history.

(56) References Cited

U.S. PATENT DOCUMENTS 9,116,219 B1    8/2015  Posse
2012/0143041 A1*  6/2012  Hirsch ................... A61B 5/055
                                                    600/411
2012/0268121 A1   10/2012  Hernando et al.

FOREIGN PATENT DOCUMENTS

JP    8131414 A     5/1996
JP    2008264014 A  11/2008
JP    2014076137 A  5/2015

OTHER PUBLICATIONS

Olafsson et al "New Approach for Estimating dR2 IN fMRI" Proceedings of ISMRM, vol. 11 Jul. 10, 2003 p. 132.
(Continued)

*Primary Examiner* — Rishi R Patel

(57) ABSTRACT

The invention provides a method of medical imaging. The method comprises: receiving, for a current active time window (204A-N) and during a brain activity analysis session (200, 500), fMRI data of a region of interest (309) of a subject (318) in an active state. A transverse relaxation, T2*, map may be generated from the fMRI data using a predefined model of fMRI data variations. The generated T2* map may be compared with a reference T2* map. A blood-oxygen-level dependent (BOLD) response of the region of interest (309) during the current active time window (204 A-N) may be estimated using the results of the comparison.

20 Claims, 4 Drawing Sheets

(51) Int. Cl.
*G01R 33/561* (2006.01)
*G01R 33/563* (2006.01)
*A61B 5/055* (2006.01)
*A61B 5/00* (2006.01)

(52) U.S. Cl.
CPC ......... *G01R 33/50* (2013.01); *G01R 33/5615* (2013.01); *G01R 33/56366* (2013.01)

(56) References Cited

OTHER PUBLICATIONS

Olafsson et al "Dynamic Update of R2 and Field Map in nMRI" Proceedings of ISMRM, vol. 12 May 1, 2004 p. 45.
Posse Stefan Ed "Multi-Echo Acquisition" Neuroimage vol. 62, No. 2, Oct. 25, 2011 p. 665-671.
Bandettini et al "Spine Echo and Gradient Echo EPI of Human Brain Activation Using Bold Contrast . . . " NMR in Biomedicine, vol. 7, No. 1-2, Mar. 1, 1994 p. 12-20.
International Search Report and Written Opinion From PCT/EP2019/081863 dated Jun. 4, 2020.
Kymberly D. Young et al "Real-Time fMRI Neurofeedback Training of Amygdala Activity in Patients with Major Depressive Disorder" PLOSone 2014.
Leena Subramanian et al Real-Time Functional Magnetic Resonance Imaging Neurofeedback for Treatment of Parkinson's Disease. , The Journal of Neuroscience, Nov. 9, 2011 • 31(45)4 6309-16317 • 16309.
Prantik Kundu "Multi-echo fMRI: A review of applications in fMRI denoising and analysis of BOLD signals" NeuroImage 154 (2017) p. 59-80.
Stefan Posse et al "A New Approach to Measure Single-Event Related Brain Activity Using Real-Time fMRI: Feasibility of Sensory, Motor, and Higher Cognitive Tasks" Human Brain Mapping 12:25-41(2001).
Fikret Işik Karahanoğlu "Transient brain activity disentangles fMRI resting-state dynamics in terms of spatially and temporally overlapping networks" Nature Communications 2015.
Xiao Liu et al "Co-activation patterns in resting-state fMRI signals" , NeuroImage 2018.
Dipasquale O, Sethi A, Laganà MM, Baglio F, Baselli G, Kundu P, et al. (2017) Comparing resting state fMRI de-noising approaches using multi- and single-echo acquisitions PLoS ONE 12(3): e0173289.
Kundu et al "Differentiating Bold and Non-Bold Signals in FMRI Time Series Using Mutli-Echo EPI" Neuromiage 60 (2012) p. 1759-1770.
Poser et al "Bold Contrast Sensitivity Enhancement and Artifact Reduction With Multecho Epi . . . " Magnetic Resonance in Med. 55 (2006) p. 1227-1235.
Posse et al "Enhancement of Bold Contrast Sensitivity by Single Shot Multi-Echo Functional MR Imaging" Magnetic Reson. in Med. 42 (1999) p. 87-97.
Seshamani et al "Robust R2 Map Estimation From Motion Scattered Slices in Fetal FMRI" (Apr. 2015) IEEE p. 845-848.
Kundu et al "Robust Resting State FMRI Processing for Studies on Typical Brain Development Based on Multi-Echo EPI Acquisition" Brain Imaging and Behavior (2015) p. 56-73.
Toshiki Iwabuchi, Measurement of brain function by fMRI: Basic and Perspective, Saitama Radiation, 2016, vol. 64 No. 3, pp. 235-243 (No translation available).

\* cited by examiner

REAL-TIME FMRI

CROSS REFERENCE TO RELATED APPLICATIONS

This application is a U.S. national phase application of International Application No. PCT/EP2019/081863 filed on Nov. 20, 2019, which claims the benefit of EP Application Serial No. 18209210.6 filed on Nov. 29, 2018 and is incorporated herein by reference.

FIELD OF THE INVENTION

The invention relates to magnetic resonance imaging, in particular to real-time fMRI.

BACKGROUND OF THE INVENTION

Magnetic resonance imaging (MRI) scanners rely on a large static magnetic field ($B_0$) to align the nuclear spins of atoms as part of the procedure for producing images within the body of a patient. These images can reflect various quantities or properties of the subject. For example, the hemodynamic response of brain activation causes magnetic and electric changes in the activated brain area. MRI allows visualizing magnetic changes, e.g. based on the cerebral blood flow or blood-oxygen-level dependent (BOLD) effect. The latter is usually referred to as functional MRI (fMRI).

A major problem in fMRI is that the BOLD signal changes are small and that there are also non-BOLD related effects that cause signal changes. The most common sources for non-BOLD signal changes are, head motion, cardiac and respiratory effects, also, scanner related artefacts cause signal changes.

Olafsson V. T. et Al: proceedings of ISMRM, vol 11, page 132 discloses a method for estimating $\Delta R2^*$ in an fMRI experiment directly from a single echo, estimate of a baseline image and a baseline $R2^*$.

Olafsson V. T. et Al: proceedings of ISMRM, vol 12, page 45 discloses a method for dynamic update of $R2^*$ and field map in fMRI.

SUMMARY OF THE INVENTION

The invention provides for a medical imaging system, a computer program product, and a method in the independent claims. Embodiments are given in the dependent claims.

Embodiments may enable detecting small fMRI signal changes. These changes are caused by a physiological response to the increased neuronal activity: the BOLD contrast. However, signal changes can also be caused by other effects, e.g. motion, cardiac and respiratory effects, scanner instabilities. It is essential to distinguish these signal changes from the changes caused by the true BOLD response. The present disclosure may enable a better BOLD contrast for real-time fMRI applications, including neurofeedback.

In one aspect the invention provides for a method of medical imaging. The method comprises: receiving, for a current active time window and during a brain activity analysis session, fMRI data of a region of interest of a subject in an active state. The method further comprises generating from the fMRI data a transverse relaxation, $T2^*$, map using a predefined model of fMRI data variations. The generated $T2^*$ map may be compared with a reference $T2^*$ map. A BOLD response of the region of interest during the current active time window may be estimated using the results of the comparison.

The region of interest may, for example, be the brain of the subject. The time window may also be referred to as a dynamic.

The method may, for example, be executed while the subject is in an active state period, wherein the current active time window is a time interval of that active state period. This may enable to identify small fMRI signal changes in real time.

The BOLD response may be used to observe different areas of the brain of the subject, which are found to be active at any given time while the subject is being under brain analysis tests.

A $T2^*$ map may, for example, be obtained from a $R2^*$ map or vice versa, where $R2^*=1/T2^*$. The present method may be configured to be executed on $R2^*$ maps as described herein with $T2^*$ map. In case of $R2^*$ maps, the logic of interpreting the BOLD response versus brain activities may be inverted in order to obtain the interpretation logic for $T2^*$ maps.

The present disclosure may enable to determine the BOLD changes for each time point individually. The BOLD changes can then be used as a feedback signal. This neurofeedback may enable that the subject can be trained to correct aberrant brain activity.

The present disclosure may, for example, enable a successful neurofeedback training as the feedback is given on true BOLD effects, e.g. the subject is not training to respond to the respiratory cycle. The $T2^*$ information is used to measure the true BOLD response and thus, giving the feedback on the real BOLD signal changes. The present disclosure may provide more insights in the functioning of the brain e.g. without giving neurofeedback, by just performing a task, variations in the activation patterns may be identified.

According to one embodiment, the method further comprises repeating the method steps during the session for each subsequent active time window. This embodiment may be advantageous as it may enable a continuous and real time analysis of the variation of the fMRI signal over longer time interval. This may enable a better modeling of the fMRI signal changes.

According to one embodiment, the method further comprises splitting the brain activity analysis session into interleaved resting state periods and active state periods of the subject, wherein the active time window occurs in an active state period of the subject that follows a resting state period. Interleaving different state periods may enable to detect both small fMRI changes between single time windows of a same state of the subject as well as global fMRI changes between periods of different states.

According to one embodiment, the resting state period immediately precedes the active state period of the current active time window.

According to one embodiment, the method further comprises receiving fMRI data obtained in a resting state period of the subject, subdividing the resting time period to a set of successive non-overlapping reference time windows, wherein a reference time window has the same length as the active time window; generating a $T2^*$ map for each determined reference time window and combining the generated $T2^*$ maps of the determined reference time windows resulting in the reference $T2^*$ map. Taking the resting state period of the present session as reference may increase the accuracy of the estimated BOLD responses e.g. compared to a case where a reference map is a theoretical one or of a map obtained from another different session.

According to one embodiment, the method further comprises excluding from the set of reference time windows a predefined subset of time windows occurring at the beginning of the resting state period, for the generating of the T2* maps. By excluding the first subset of dynamics of the resting state period, the BOLD response delay from a previous active state period may not interfere with the BOLD responses used for the generation of the reference T2* map. This may further increase the accuracy of the estimated BOLD responses. The subset of time windows may, for example, comprise 3 time windows of 2 second each.

According to one embodiment, the method further comprises performing the method steps for each voxel in the fMRI data, wherein the comparison is performed between T2* value of each voxel of the generated T2* map and the T2* value of the same voxel in the T2* reference map. This may enable to identify specific small areas of the brain that are active.

According to one embodiment, the fMRI data comprises multiple echo image data obtained at respective echo times, TE, wherein generating the T2* map comprises fitting the T2* values variations over the echo time using the following model:

$$S(TE) = S_0 e^{\frac{-TE}{T_2^*}},$$

where TE is the echo time and S0 is the signal at TE=0. This may enable an accurate estimate of the T2* values. This model may be advantageous because it separates between changes in S0 which are non-BOLD variations of the signal intensity from the real BOLD variations that are encoded in T2* variations. Changes in $S_0$ can be caused by motion, cardiac and respiratory effects. Also scanner instabilities contribute to variations in $S_0$.

According to one embodiment, the BOLD response is indicative of an active state of a portion of the region of interest whose associated voxel has a T2* value of the T2* map higher than the reference T2* value of that voxel, and the BOLD response being indicative of a resting state of a portion of the region of interest whose associated voxel has a T2* value of the T2* map smaller than the reference T2* value of that voxel.

According to one embodiment, the fMRI data comprises a plurality of MRI images at a plurality of different echo times following an application of an excitation RF pulse.

In another aspect the invention further provides for a computer program product comprising machine executable instructions for execution by a processor, wherein execution of the machine executable instructions causes the processor to perform the methods of any of the preceding embodiments.

In another aspect, the invention further provides for a medical imaging system comprising: a memory for storing machine executable instructions; and a processor for controlling the medical imaging system, wherein execution of the machine executable instructions causes the processor to: receive, for a current active time window and during a brain activity analysis session, fMRI data of a region of interest of a subject in an active state; generate from the fMRI data a transverse relaxation, T2*, map using a predefined model of fMRI data variations; compare the generated T2* map with a reference T2* map; estimate a blood-oxygen-level dependent (BOLD) response of the region of interest during the current active time window using the results of the comparison.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a 'circuit,' 'module' or 'system'. Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, random access memory (RAM), read only memory (ROM), an optical disk, a magneto-optical disk, and the register file of the processor. Examples of optical disks include compact disks (CD) and digital versatile disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising a 'processor' should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as C or similar programming languages and compiled into machine executable instructions. In some instances, the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the internet using an internet service provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE 488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, a tactile electronic display, a Braille screen, a cathode ray tube (CRT), a storage tube, a bi-stable display, an electronic paper, a vector display, a flat panel display, a vacuum fluorescent display (VF), light-emitting diode (LED) displays, an electroluminescent display (ELD), plasma display panels (PDP), a liquid crystal display (LCD), organic light-emitting diode displays (OLED), a projector, and a head-mounted display.

Magnetic Resonance imaging data is defined herein as being the recorded measurements of radio frequency signals emitted by atomic spins using the antenna of a magnetic resonance apparatus during an MRI scan. Magnetic resonance image data is defined herein as being the reconstructed two-dimensional or three-dimensional visualization of anatomic data that is reconstructed from the magnetic resonance k-space data. Visualization of the magnetic resonance image data can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
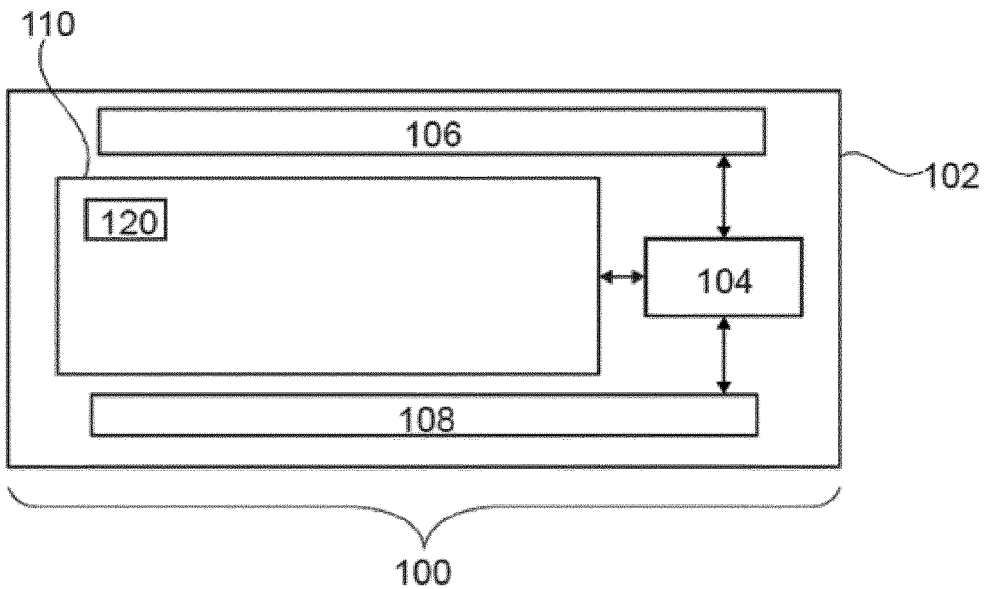
FIG. 1 illustrates an example of a medical imaging system.

FIG. 1 illustrates an example of a medical imaging system 100 a general suited for implementing method steps as involved in the present disclosure. The medical imaging system 100 is shown as comprising a computer 102 that comprises a processor 104. The processor is shown as being connected to an optional hardware interface 106, and an optional user interface 108. The user interface 108 may be or include a display for rendering images. The hardware interface 106 may, for example, be a network interface or it may also be used for exchanging data or commands with other components of the medical imaging system. The processor 104 is further shown as being connected to a memory 110. The memory 110 may be any combination of memory which is accessible to the processor 104. This may include such things as main memory, cached memory, and also non-volatile memory such as flash RAM, hard drives, or other storage devices. In some examples the memory 104 may be considered to be a non-transitory computer-readable medium.

The memory 110 is shown as containing machine-executable instructions 120. The machine-executable instructions 120 enable the processor 104 to perform various data processing tasks and also in some examples to control other components of the medical imaging system 100. The machine-executable instructions 120 enable the processor 104 to perform at least part of the present method.

The methods described herein may be in the form of a source program, executable program (object code), script, or any other entity comprising a set of instructions to be performed. When a source program, then the program needs to be translated via a compiler, assembler, interpreter, or the like, which may or may not be included within the memory 110, so as to operate properly in connection with an OS. Furthermore, the methods can be written as an object oriented programming language, which has classes of data and methods, or a procedure programming language, which has routines, subroutines, and/or functions.

Figure 2:
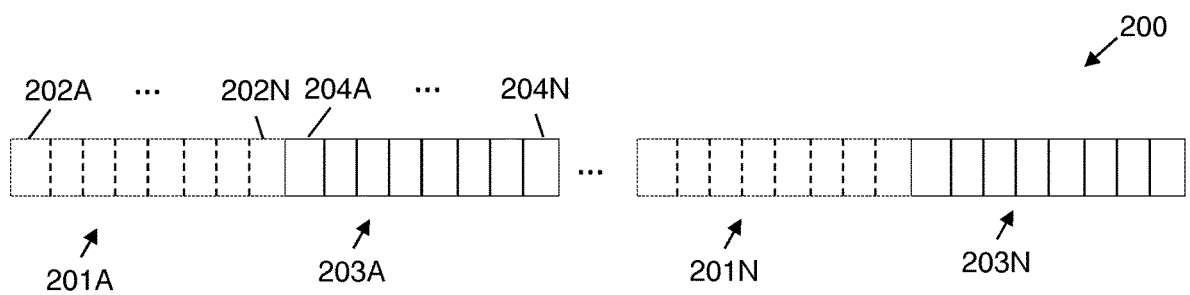
FIG. 2 depicts a succession of time periods of a brain activity analysis session.

FIG. 2 depicts a succession of time periods of a brain activity analysis session 200. The brain activity analysis session 200 may be split or comprise interleaved resting state periods 201A-N (indicated with dashed lines) and active state periods 203A-N (indicated with solid lines) of the subject. During the resting state periods 201A-N, the subject is in resting state indicating that his or her brain is not performing a specific task. During the active state periods 203A-N, the subject is performing an activity such as watching a video, and thus parts of his or her brain may be active.

Each of the resting state periods 201A-N is subdivided into resting time windows 202A-202N of equal duration. Each of the active state periods 203A-N is subdivided into active time windows 204A-204N of equal duration. The active time windows 204A-N have the same duration as the resting time windows 202A-N. Only time windows of one resting state period and one active state period are shown for clarity purpose.

For example, the subject may have to perform a silent word generation task during active state periods. The brain activity analysis session 200 may, for example, consist of 32 s resting state periods interleaved with 32 s active state periods. The total scan duration of the brain activity analysis session 200 may, for example, be 416 second, resulting in 7 resting state periods, interleaved with 6 active state periods of 16 time windows each.

The brain activity analysis session 200, as defined in FIG. 2, may enable an accurate measurement of the BOLD response in real time e.g. while the subject is under the defined states.

The time granularity of the resting state periods, active state periods and brain activity analysis session are provided for exemplification purpose. The skilled person in the art would understand that other configurations of brain activity analysis sessions such as different time window durations etc. may be used with the present method.

Figure 3:
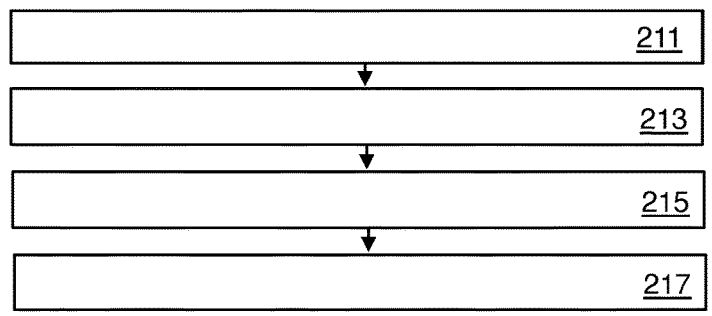
FIG. 3 is a flowchart for a method for medical imaging.

FIG. 3 is a flowchart of a method for medical imaging. In step 211, fMRI data of a region of interest of a subject in an active state may be received. The fMRI data are received for a current active time window e.g. 204B and during the brain activity analysis session 200. The current time window 204B may be part of an active state period during which the subject is currently performing an activity e.g. the method of FIG. 3 being performed in real time. An example fMRI data acquisition is provided in FIG. 5A.

In step 213, a transverse relaxation, T2*, map may be generated from the fMRI data using a predefined model of fMRI data variations. The model may describe the variation of the acquired signals as function of TE. One example model may describe a signal decay for each multi echo acquisition as follows:

$$S(TE) = S_0 e^{\frac{-TE}{T_2^*}},$$

where TE is the echo time and $S_0$ is the signal at TE=0.

In step 215, the generated T2* map may be compared with a reference T2* map. The reference T2* map may, for example, be obtained as follows.

Reference fMRI data may be obtained during a resting state period e.g. 201A of the subject. A T2* map may be generated for each resting time window 202A-N of the resting state period. The generated T2* maps may be combined resulting in the reference T2* map. The fMRI data are considered as reference data because they are acquired during a resting state period of the subject. An example of determining the reference map is described in FIG. 5A.

In step 217, a BOLD response of the region of interest during the current active time window may be estimated using the results of the comparison. The changes in T2* values are related to the BOLD variations. A T2* value increases regionally as a result of the BOLD response in activated areas. The changes in $S_0$ contain non-BOLD variations of the signal intensity which can be caused by motion, cardiac and respiratory effects. Also scanner instabilities (e.g. of the imaging system 300) contribute to variations in $S_0$.

In one example, steps 213-217 may be executed voxel-wise. That is, for each voxel of the fMRI data, the T2* value may be generated by, for example, fitting the model to the voxel values as function of the echo time TE (e.g. if 10 echo times are used, 10 voxel values may be fitted). This results in T2* values (T2* map) for voxels of the fMRI data. For each voxel of the fMRI data, a comparison is performed between the T2* value of the voxel and the reference T2* value of the same voxel and the BOLD response may be estimated for the voxel by based on that comparison result.

The method as described herein may, for example, be performed on fMRI data in the native space. The received fMRI data may be acquired in the subject's native space.

Figure 4:
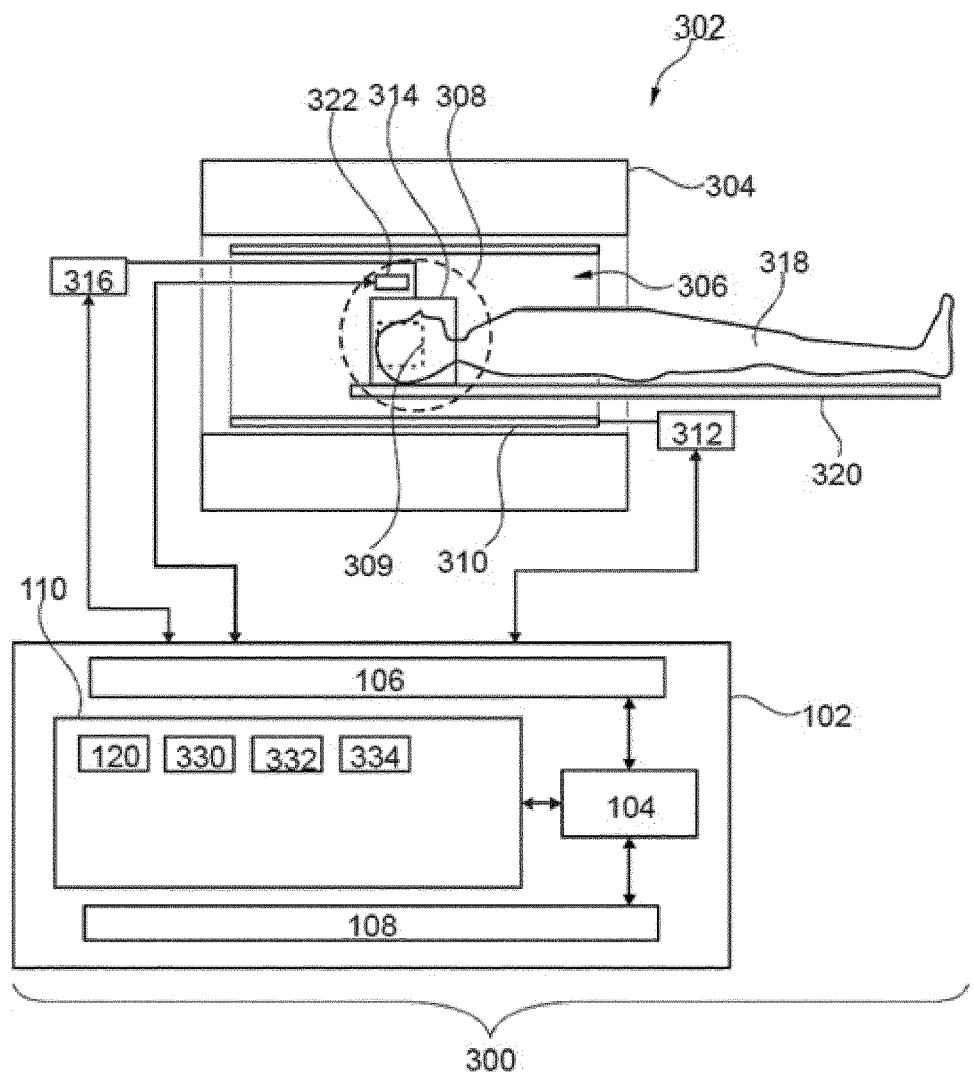
FIG. 4 illustrates a further example of a medical imaging system.

FIG. 4 illustrates a further example of a medical imaging system 300. The medical imaging system 300 in FIG. 4 is similar to the medical imaging system 100 of FIG. 1 with the exception that the medical imaging system 300 also comprises a magnetic resonance imaging system.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging. A region of interest 309 is shown within the imaging zone 308. The magnetic resonance data that is acquired typically acquired for the region of interest. A subject 318 is shown as being supported by a subject support 320 such that at least a portion of the subject 318 is within the imaging zone 308 and the region of interest 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 are connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. In this example the radio-frequency coil 314 is a head coil and the region of interest 309 images the brain of the subject 318.

The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receiver. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

Within the bore 306 of the magnet 304 there is a subject indicator 322. The subject indicator may, for example, provide an audio and/or visual stimulus to the subject 318. The subject indicator 322 is able to provide a stimulus in one of two different distinct states; an active state and a resting state. When the subject indicator 322 shows an active state the subject 318 either thinks particular thoughts or performs particular physical activity such as moving a limb or performing another action. The subject indicator 322 could, for example, have a light which is visible to the subject 318, be a display, or provide an audio signal. The transceiver 316, the gradient controller 312, and the subject indicator 322 are shown as being connected to the hardware interface 106 of the computer system 102.

The memory 110 is further shown as containing the pulse sequence commands 330. The pulse sequence commands are either commands or data which can be converted into such commands which enable the processor 104 to control the magnetic resonance imaging system 302. The memory 110 is further shown as containing magnetic resonance imaging data 332 that was acquired by controlling the magnetic resonance imaging system 302 with the pulse sequence commands 330. The pulse sequence commands 330 may also contain instructions which cause the subject indicator 322 to change between indicating the active and resting state during individual acquisitions of the magnetic resonance imaging data 332. Data which can be used to determine later which state the magnetic resonance imaging data 332 is in the meta data 334. The meta data 334 is shown as being stored in the memory 110.

Figure 5A:
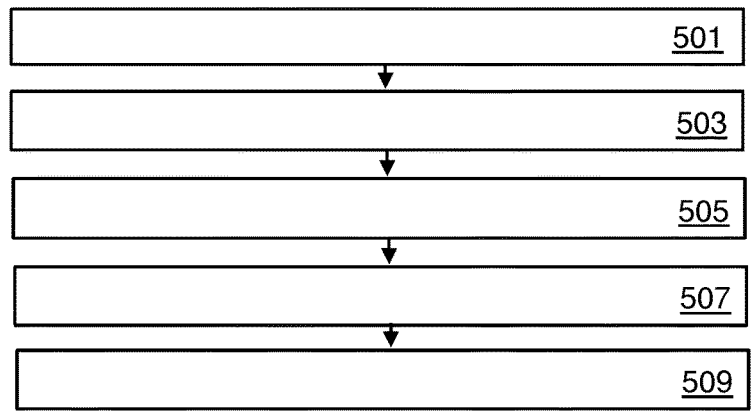
FIG. 5A is a flowchart of a method for estimating BOLD responses in accordance with an example of the present disclosure.

FIG. 5a is a flowchart of a method for estimating BOLD responses in accordance with an example of the present disclosure. In this example, the subject 318 had to perform a silent word generation task during active state periods of a brain activity analysis session 500. The experiment consisted of 32 s resting state periods interleaved with 32 s active state periods. The total scan duration was 416 second, resulting in seven resting state periods, interleaved with six active state periods of 16 time windows each.

In step 501, fMRI data is acquired (e.g. by imaging system 300) with a multi-echo EPI sequence. Using multi-echo EPI sequences may enable a more detailed analysis of the brain activity. An example of multi echo data may be acquired with echo times of 12, 35 and 58 ms, respectively, for each time window of resting state periods and active state periods of the brain activity analysis session 500. The repetition time TR is, for example, 2000 ms. During each TR a full brain volume is recorded, for example 27 slices, wherein each slice has a resolution of 64×64. This may be used for generating fMRI data while the subject is performing a task, for example, silent word generation. This may enable to evaluate Brain activation during silent word generation using the fMRI data. Other resolutions are possible.

The signal decay for each multi echo acquisition is described by model equation $$S(TE) = S_0 e^{\frac{-TE}{T_2^*}},$$

where TE is the echo time and $S_0$ is the signal at TE=0. The changes in T2* are related to the BOLD variations. The T2* increases regionally as a result of the BOLD response in activated areas. The changes in $S_0$ are non-BOLD variations of the signal intensity which can be caused by motion, cardiac and respiratory effects. Also scanner instabilities contribute to variations in $S_0$.

The model equation is fitted in step 503 to the measured signals per voxel of the acquired fMRI data and $S_0$ and T2* maps are generated. The fitting may, for example, be done in Matlab, using the Matlab function 'fit'. A single exponential ('Exp1') was fitted with additional fitting options: 'TolFun', 0.1, 'TolX', 0.1, 'MaxFunEvals', 100, 'MaxIter', 10. A R2* map may, for example, be generated from T2* map because R2* is the inverse of the T2*: R2*=1/T2*. This means that BOLD related signals will have shorter R2*. An example of a multi-echo acquisition and the derived S0 and R2* maps is show in FIG. 5B.

Before performing the fitting step 503, the fMRI data may be pre-processed using known pre-processing methods such as realignment. For example, the individual echo data are realigned and smoothed e.g. using spatial smoothing (SPM), such that the fit of step 503 is performed on the realigned and smoothed echo data to get the S0 and the T2*.

In step 507, the R2*series is analyzed with the aim to determine the task activation per time window. For each resting state period 530, the average R2* is determined over a series of time windows 532 as indicated in FIG. 5C. The first 3 time windows (6 seconds) 531 are not used, because BOLD effects from the preceding active state period 529 might still be active. In step 509, for each individual active state time window of sub interval 537 the active state period 535, the percentage signals change (PSC) of the R2* was determined. Again the first 3 time windows 536 are not used because of the BOLD response delay. This is illustrated in FIG. 5C, where line 539 indicates the BOLD response of the subject during the session 500.

For each voxel of the fMRI data, the mean of the R2* values of the voxel dynamic (j) in the time windows 532 are averaged according to average equation $$\overline{rest_i} = \frac{\sum_{j=i+3}^{j=i+15} dynamic(j)}{n},$$

where i is the first time window of the resting state period 530 and n is the number of time windows 532 and j is a time window of the time windows 532. $\overline{rest_i}$ is a reference R2* value for a given voxel obtained using the resting state time period 530.

As indicated in FIG. 5C, the start windows for the resting state periods are=1, 33, 65, 97, 129, 161, 193, respectively. The Percentage-Signal-Change per active state time window may be defined by PSC equation:

$$PSC_t = \frac{task(t) - \overline{rest_i}}{\overline{rest_i}} \times 100,$$

where $\overline{rest_i}$ is calculated according to the average equation and task (t) are the individual active state time windows of the active state period 535 that immediately follows the resting state time period 530 that is used to calculate the value $\overline{rest_i}$. task(t) is the actual or current R2* value for a given voxel obtained using the a current time window of the active state time period 535. In one example, the PSC may be calculated only for predefined voxels. The predefined voxels may be selected using a mask. In one example, a mask may be used on the grey matter such that the PSC is calculated only for voxels within the mask. Other examples of masks may be used as well. For example, the whole brain mask or a mask of grey and white matter.

According to the PSC equation, each activation per active state time window, is defined as the $PSC_t$ with respect to the previous resting state period. Two effects may be distinguished, namely a BOLD positive effect and BOLD negative effect. According to the BOLD positive effect, the R2* value of a given voxel in the current active state time window decreases (e.g. task(t)<$\overline{rest_i}$ for the given voxel) indicating that the BOLD effect of the time window has increased with respect to the mean of the resting state period. This indicates an activation. According to the BOLD negative effect, the R2* value of a given voxel increases (e.g. task(t)>$\overline{rest_i}$ for the given voxel) indicating that the BOLD effect has decreased with respect to the mean of the resting state period. This indicates a deactivation. Deactivation means that these voxels show a decreased BOLD effect.

Regarding the positive BOLD effect (activation), the R2* change of the active state time window 89 of the active state time period 537 is calculated according to average and PSC equations, i.e. the $\overline{rest_i}$ was calculated for resting state time windows 36-48. The BOLD response of echo-2 was also calculated in SPM using the whole data set (after realignment and smoothing). The comparison is shown in FIG. 5D. As shown in FIG. 5D, the activation patterns for active state time window 89 are very similar to the BOLD responses found in SPM. In SPM a GLM function is applied to the complete data set, all 208 time windows, therefore, resulting in a better statistical power. Similar activation patterns as found for active state time window 89 were found in a significant number of dynamics. Long term scanner effects can probably be excluded since the activation was calculated with respect to the mean of the directly preceding resting block.

Figure 5B:
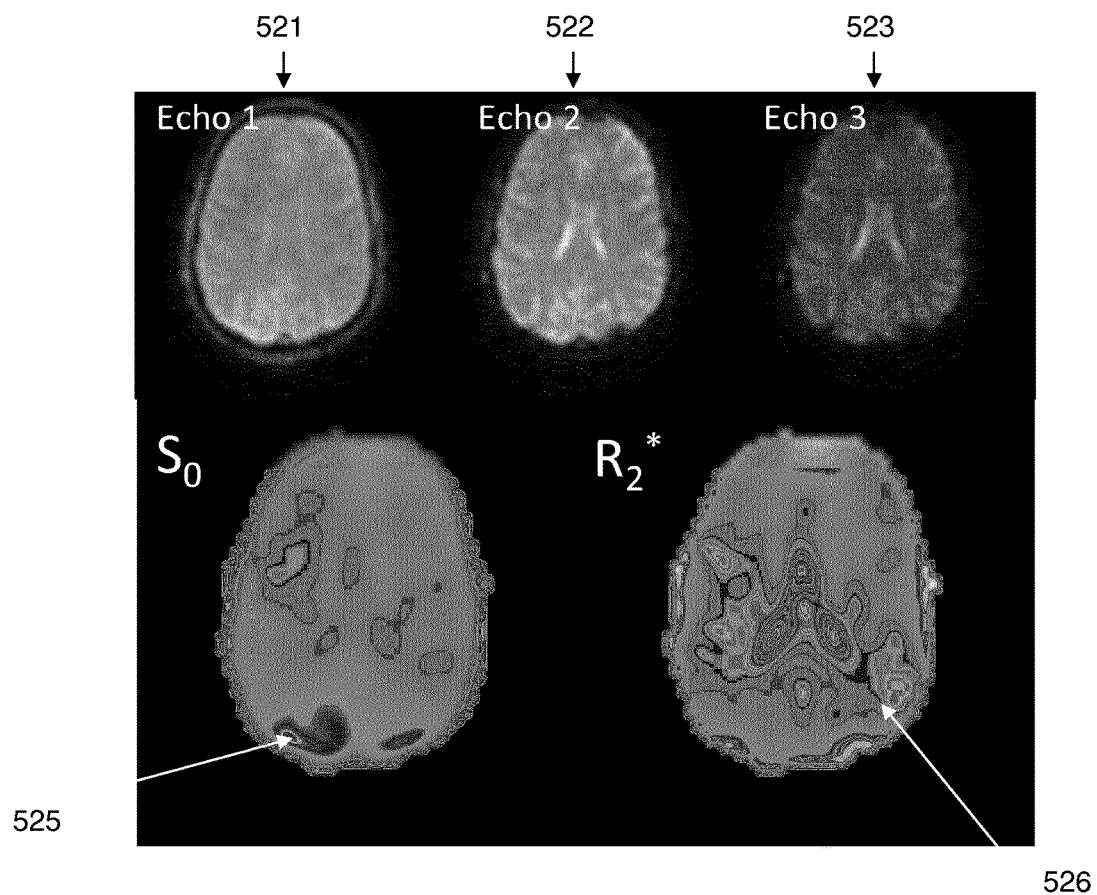
FIG. 5B shows multi-echo acquisition images and the derived S0 and R2* maps.
Figure 5C:
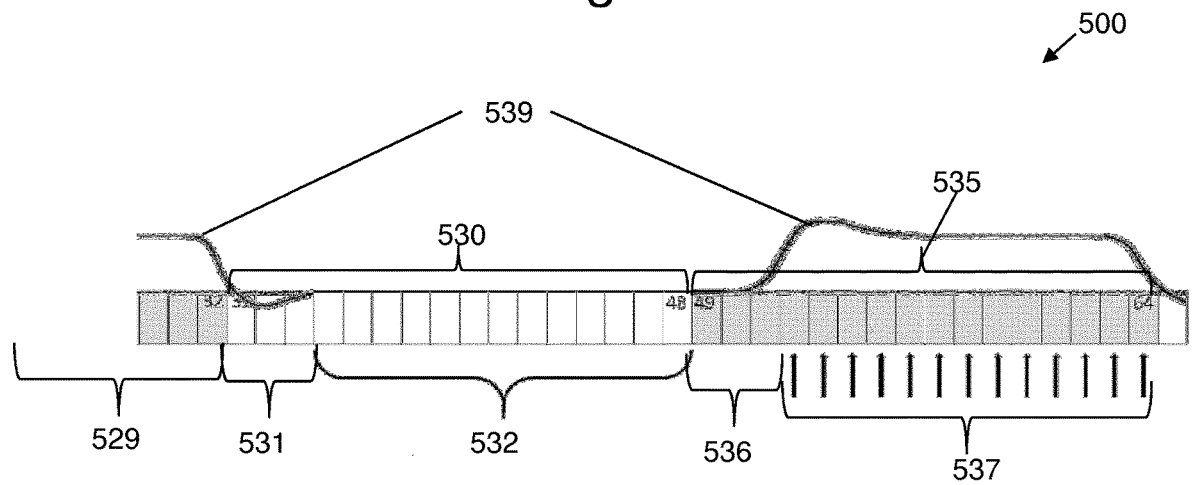
FIG. 5C depicts a succession of time periods of a brain activity analysis session.
Figure 5D:
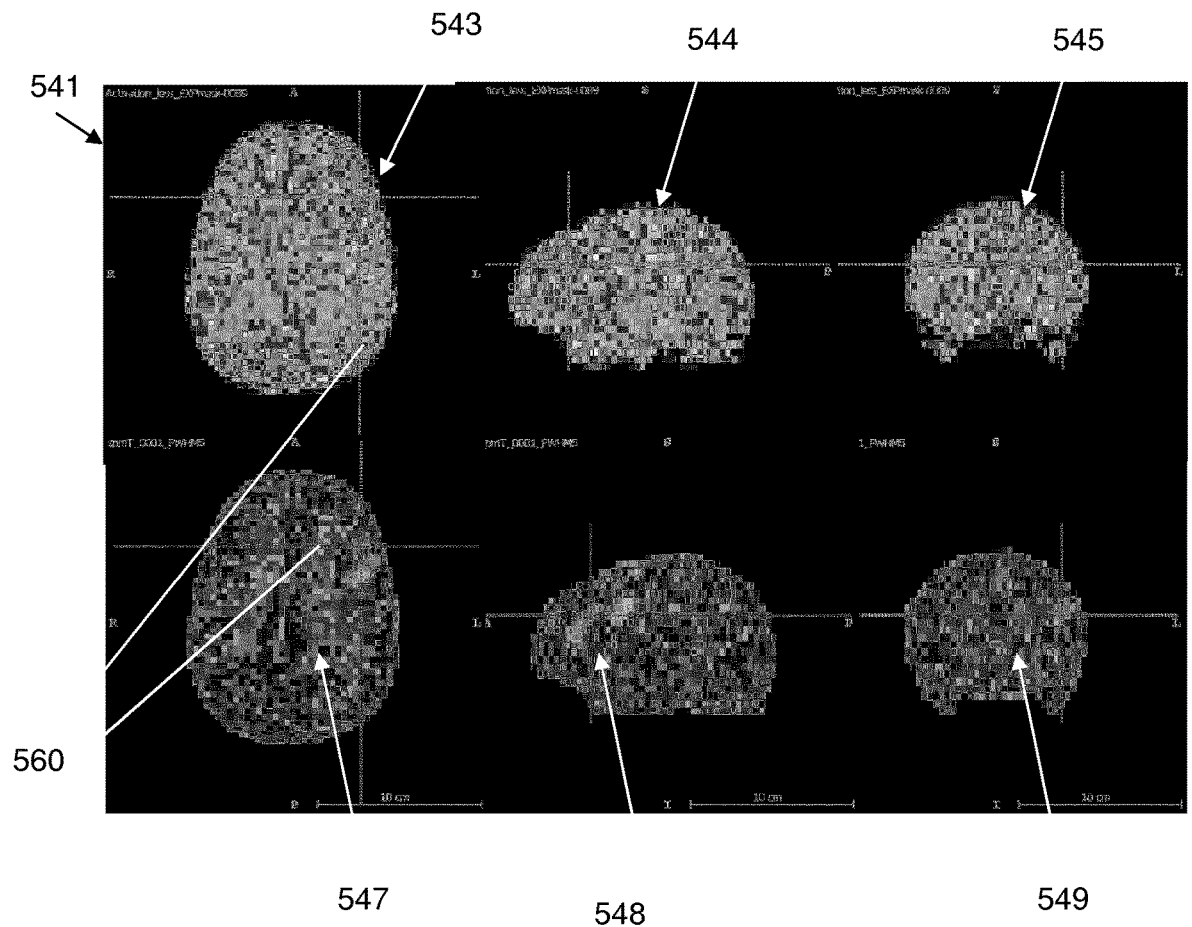
FIG. 5D shows BOLD response maps.

FIG. 5B shows MR images 521-523 of a slice (13) of fMRI data acquired during an active state time window 89 of the active state time period 535. The MR images 521, 522 and 523 are reconstructed of fMRI data obtained using three echoes with TE=12, 35 and 58 ms respectively. FIG. 5C further shows the $S_0$ map 525 and R2*map 525 that is derived from the images 521-523 as described above by fitting for each voxel the model equation to three voxel values of the three echoes.

FIG. 5D shows the positive activation pattern 541 calculated for active state time window 89. The activation pattern 541 comprises a map of BOLD responses 543, 544 and 545 obtained for different slices, namely axial 13, sagittal 46 and coronal 39 respectively. FIG. 5D further shows the BOLD responses 547, 548 and 549 calculated for the second echo 522 using SPM for the three slices. Lines 560 indicate slice positions.

LIST OF REFERENCE NUMERALS 100 medical imaging system
102 computer
104 processor
106 hardware interface
108 user interface
110 computer memory
120 machine executable instructions
200 brain activity analysis session
201 resting state time period
202 resting state time window
203 active state time period
204 active state time window
211-217 steps
300 medical imaging system
302 magnetic resonance imaging system
304 magnet
306 bore of magnet
308 imaging zone
309 region of interest
310 magnetic field gradient coils
312 magnetic field gradient coil power supply
314 radio-frequency coil
316 transceiver
318 subject
320 subject support
322 subject indicator
330 pulse sequence commands
332 magnetic resonance imaging data
334 metadata
500 brain activity analysis session
501-509 steps.
521-523 MR images
525 S0 map
526 R2* map
529 active state period
530 resting state time period
531 resting state time windows
532 resting state time windows
535 active state time period
536 active state time windows
537 active state time windows
539 BOLD response
541 activation pattern
543-545 BOLD response maps
547-549 BOLD response maps with SPM
560 lines.

The invention claimed is:

1. A method of medical imaging, comprising:
receiving, for a current active time window and during a brain activity analysis session, fMRI data of a region of interest of a subject in an active state;
generating from the fMRI data a transverse relaxation, a generated T2* map using a predefined model of fMRI data variations;
comparing the generated T2* map with a reference T2* map;
estimating a blood-oxygen-level dependent (BOLD) response of the region of interest during the current active time window using results of the comparison;
receiving fMRI data obtained in a resting state period of the subject, subdividing the resting state period to a set of successive non-overlapping reference time windows, wherein a reference time window has a same length as the current active time window;
generating a T2* map for each determined reference time window and combining the generated T2* maps of each of the determined reference time windows resulting in the reference T2* map; and
excluding from the set of reference time windows a predefined subset of time windows occurring at a beginning of the resting state period, for the generating of the T2* maps, wherein a BOLD response delay from a previous active state period does not interfere with the BOLD response used for the generation of the reference T2* map.

2. The method of claim 1, further comprising repeating the method during the brain activity analysis session for each subsequent active time window.

3. The method of claim 1, further comprising splitting the brain activity analysis session into interleaved resting state periods and active state periods of the subject, wherein the active time window occurs in an active state period of the subject that follows a resting state period.

4. The method of claim 3, wherein the resting state period immediately precedes the active state period of the current active time window.

5. The method of claim 1, further comprising performing the method steps for each voxel in the fMRI data, wherein the comparison is performed between T2* value of each voxel of the generated T2* map and the T2* value of the same voxel in the T2* reference map.

6. The method of claim 1, the fMRI data comprising multiple echo image data obtained at respective echo times, TE, wherein the generated T2* map comprises fitting T2* values variations over the echo time using the following model:

$$S(TE) = S_0 e^{\frac{-TE}{T_2^*}},$$

where TE is the echo time and $S_0$ is the signal at TE=0.

7. The method of claim 1, the BOLD response being indicative of an active state of a portion of the region of interest whose associated voxel has a T2* value higher than a reference T2* value of that voxel, and the BOLD response being indicative of a resting state of a portion of the region of interest whose associated voxel has a T2* value smaller than a reference T2* value of that voxel.

8. The method of claim 1, the fMRI data comprising a plurality of MRI images at a plurality of different echo times following an application of an excitation RF pulse.

9. A medical imaging system comprising:
a memory storing machine executable instructions; and
a processor for controlling the medical imaging system, wherein execution of the machine executable instructions causes the processor to:

receive, for a current active time window and during a brain activity analysis session, fMRI data of a region of interest of a subject in an active state;

generate from the fMRI data a transverse relaxation, a generated T2* map using a predefined model of fMRI data variations;

compare the generated T2* map with a reference T2* map;

estimate a blood-oxygen-level dependent (BOLD) response of the region of interest during the current active time window using results of the comparison;

receive fMRI data obtained in a resting state period of the subject, subdividing the resting state period to a set of successive non-overlapping reference time windows, wherein a reference time window has a same length as the current active time window;

generate a T2* map for each determined reference time window and combining the generated T2* maps of the each of the determined reference time windows resulting in the reference T2* map; and exclude from the set of reference time windows a predefined subset of time windows occurring at a beginning of the resting state period, for the generating of the T2* maps, wherein a BOLD response delay from a previous active state period does not interfere with the BOLD response used for the generation of the reference T2* map.

10. A magnetic resonance imaging (MRI) system comprising the medical analysis system of claim 9, the MRI system being configured for acquiring fMRI data using an imaging protocol provided by the medical analysis system.

11. The MRI system of claim 10, being configured for applying an excitation RF pulse; and obtaining a plurality of MRI images at a plurality of different echo following application of the excitation RF pulse.

12. The medical imaging system of claim 9, wherein the instructions further cause the processor to split the brain activity analysis session into interleaved resting state periods and active state periods of the subject, and the active time window occurs in an active state period of the subject that follows a resting state period.

13. The medical imaging system of claim 12, wherein the resting state period immediately precedes the active state period of the current active time window.

14. The medical imaging system of claim 9, the BOLD response being indicative of an active state of a portion of the region of interest whose associated voxel has a T2* value higher than a reference T2* value of that voxel, and the BOLD response being indicative of a resting state of a portion of the region of interest whose associated voxel has a T2* value smaller than a reference T2* value of that voxel.

15. The medical imaging system of claim 9, wherein the fMRI data comprises a plurality of MRI images at a plurality of different echo times following an application of an excitation RF pulse.

16. A tangible, non-transitory computer readable medium that stores instructions, which when executed by a processor, cause the processor to:

receive, for a current active time window and during a brain activity analysis session, fMRI data of a region of interest of a subject in an active state;

generate from the fMRI data a transverse relaxation, a generated T2* map using a predefined model of fMRI data variations;

compare the generated T2* map with a reference T2* map;

estimate a blood-oxygen-level dependent (BOLD) response of the region of interest during the current active time window using results of the comparison;

receive fMRI data obtained in a resting state period of the subject, subdividing the resting time period to a set of successive non-overlapping reference time windows, wherein a reference time window has a same length as the current active time window;

generate a T2* map for each determined reference time window and combining the generated T2* maps of each of the determined reference time windows resulting in the reference T2* map; and exclude from the set of reference time windows a predefined subset of time windows occurring at a beginning of the resting state period, for the generating of the T2* maps, wherein a BOLD response delay from a previous active state period does not interfere with the BOLD response used for the generation of the reference T2* map.

17. The tangible, non-transitory computer readable medium of claim 16 that stores instructions, which when executed by the processor, further cause the processor to acquire fMRI data using an imaging protocol provided by the medical analysis system.

18. The tangible, non-transitory computer readable medium of claim 17 that stores instructions, which when executed by the processor, further cause the processor to apply an excitation RF pulse; and obtain a plurality of MRI images at a plurality of different echo following application of the excitation RF pulse.

19. The tangible, non-transitory computer readable medium of claim 17 that stores instructions, which when executed by the processor, further cause the processor to split the brain activity analysis session into interleaved resting state periods and active state periods of the subject, wherein the active time window occurs in an active state period of the subject that follows a resting state period.

20. The tangible, non-transitory computer readable medium of claim 17 that stores instructions, wherein the BOLD response is indicative of an active state of a portion of the region of interest whose associated voxel has a T2* value higher than a reference T2* value of that voxel, and the BOLD response is indicative of a resting state of a portion of the region of interest whose associated voxel has a T2* value smaller than the reference T2* value of that voxel.

* * * * *